United States Patent
Li et al.

(10) Patent No.: US 8,106,356 B2
(45) Date of Patent: Jan. 31, 2012

(54) BETA-RAY SOOT CONCENTRATION DIRECT READOUT MONITOR AND METHOD FOR DETERMINING EFFECTIVE SAMPLE

(75) Inventors: Hongjie Li, Wuhan (CN); Hanyong Yao, Wuhan (CN); Zhongquan Chen, Wuhan (CN)

(73) Assignee: Wuhan Tianhong Instruments Co. Ltd. (CN)

( * ) Notice: Subject to any disclaimer, the term of this patent is extended or adjusted under 35 U.S.C. 154(b) by 511 days.

(21) Appl. No.: 12/442,804

(22) PCT Filed: Jun. 20, 2008

(86) PCT No.: PCT/CN2008/071397
§ 371 (c)(1), (2), (4) Date: Mar. 25, 2009

(87) PCT Pub. No.: WO2009/003390
PCT Pub. Date: Jan. 8, 2009

(65) Prior Publication Data
US 2009/0321635 A1 Dec. 31, 2009

(30) Foreign Application Priority Data
Jul. 3, 2007 (CN) .......................... 2007 1 0122913

(51) Int. Cl.
*G01N 23/06* (2006.01)
(52) U.S. Cl. ...................................................... 250/307
(58) Field of Classification Search .................. 250/306, 250/307; 73/28.01, 863.23
See application file for complete search history.

(56) References Cited

U.S. PATENT DOCUMENTS 5,349,844 A * 9/1994 Lilienfeld ..................... 73/28.01
7,111,496 B1 * 9/2006 Lilienfeld et al. ............ 73/28.01

FOREIGN PATENT DOCUMENTS

| CN | 1108764 A | 9/1995 |
|---|---|---|
| CN | 2548153 | 4/2003 |
| CN | 101101256 A | 1/2008 |
| CN | 201060154 Y | 5/2008 |
| JP | 57-128830 A | 8/1982 |
| JP | 2001066266 A * | 3/2001 |
| JP | 2003-139725 A | 5/2003 |
| JP | 2006-003090 A | 1/2006 |

* cited by examiner

*Primary Examiner* — David Porta
*Assistant Examiner* — Marcus Taningco
(74) *Attorney, Agent, or Firm* — Workman Nydegger

(57) ABSTRACT

A beta-ray soot concentration direct readout monitor and a method for determining effective sample. The monitor includes a fume collection cell and a fume mass detection cell. The fume collection cell includes a fume sampling gun, a filter paper and a mechanical control auto form feed structure. The fume sampling gun includes a gathering tube, a pitot tube and a sheath tube. The gathering tube tail of the fume sampling gun is equipped with an upper cavity body and a corresponding lower cavity body. The filter paper passes through space between the upper and lower cavity bodies. A paper supporting gate is provided at the inlet of the lower cavity body. A smoke outlet is equipped at a lower part of the lower cavity body. The sampling area of the soot acquired from the upper cavity body is at least twice with the actual testing area of the filter paper.

6 Claims, 6 Drawing Sheets

BETA-RAY SOOT CONCENTRATION DIRECT READOUT MONITOR AND METHOD FOR DETERMINING EFFECTIVE SAMPLE

TECHNICAL FIELD OF THE INVENTION

The present invention involves a detecting instrument for environment protection use, especially relates to a β-ray soot concentration direct-reading monitor capable of increasing the accuracy of measurement and a method concerning the determination on whether a sample obtained by the monitor is effective.

BACKGROUND OF THE INVENTION

The environment pollutions caused by pollution sources such as industrial boilers, power plant boilers and industrial furnace, or the like are very severe nowadays, and thus countries all over the world are diving to the relevant researches for the purpose of controlling those pollutions. As a result, there is a need of monitoring the concentration of particulate matter emitted by those pollution sources. At present, common monitoring methods include opacity method, light transmission method, laser back-scattering method, triboelectric-method, and β-ray absorption method (testing inside a flue), etc.

In these methods, filtrating-weighing method is employed most broadly nowadays. The basic principle of this method is: a certain volume dust-containing smoke passes through a filter cylinder with known weight where dust particulates in the smoke are stopped and deposited such that the soot concentration can be calculated according to the weight difference of the filter cylinder before and after sampling and the volume of sampling. Since the smoke in flue has a certain flow rate and pressure as well as a pretty high temperature and humidity, and often contains some erosive gas, an isokinetic sampling method must be employed here. Many nations take filtrating-weighing method as a standard method because of its high accuracy and good precision. Similarly, China also selects this method as the standard of appraising other analysis methods. With reference to FIG. 1, it is a diagram of the internal structure of a β-ray soot concentration direct-reading monitor in the prior art, which comprises: a soot collection unit and a soot mass detection unit, and said soot collection unit comprises a soot sampling gun, a filter paper and a mechanical-control auto filter paper feeding structure, wherein said soot sampling gun includes a gathering tube 11, a Pitot tube and a sheath tube. The soot passing through the gathering tube directly covers on the filter paper 3 and then is analyzed by means of a β-ray source 52.

The Chinese patent numbered 02238238.0 disclosed a β-ray particulates emission continuous monitor, characterizing in that it includes a cantilever sampling tube, a compressor, a filter paper and a filter paper feeding device, a β-ray source (carbon 14 source), a β-ray receiving Geiger-Muller detector, a S Pitot tube, a computer-based data processing device and a casing. The sampling tube of this β-ray particulates emission continuous monitor is connected to a negative pressure source. The filter paper is drawn by the filter paper feeding device to pass through the cross section of the sampling tube, and then pass between the β-ray source and the β-ray receiving GEIGER-MULLER detector. The β-ray receiving GEIGER-MULLER detector is electrically connected with the computer-based data processing device. The S Pitot tube is connected by pipes with the compressor. A temperature sensor also is electrically connected with the computer-based data processing device. With reference to FIG. 2, it is a structural diagram of the soot sampling gun of a β-ray soot concentration direct-reading monitor in the prior art. As depicted in FIG. 2, sampling tube 11 and Pitot tube 12 are respectively housed in two sheath tubes 13' and 13". In this design of the monitor, a heating tube 45 and said sampling tube 11 are provided in the same sheath tube 13' to heat the soot. However, since the heat provided by the heating tube is not uniform, not only the dehumidifying effect is not obvious but also a reflux condensation is easily caused. Thereby, the heating process loses its value.

To sum up, the present available β-ray soot concentration monitor still has following drawbacks which need to be conquered:

in the case where the sampling acreage is equal to the testing acreage, the mass overflow of the sampling acreage is occurred, the soot is of high humidity and thus effects the detection of the soot mass, the detection of the soot with high dispersion (wide-spread distribution??) and large particulate is not accurate because the β-rays emitted from the β-ray source (carbon 14 source) are absorbed completely by soot rather than able to penetrate this kind of the soot at all.

In order to overcome the problems above mentioned, the inventor conducted research and experimentation for a long time and achieved the present invention.

THE SUMMARY OF THE INVENTION

The objective of the present invention is to provide a β-ray soot concentration direct-reading monitor and a method for determining effective sample thereof to overcome the above drawbacks of monitors in the prior art.

In order to carry out the above objective, the present invention uses the following technical solution. First of all, a β-ray soot concentration direct-reading monitor is provided, which comprises a soot collection unit and a soot mass detection unit. Said soot collection unit includes a soot sampling gun, a filter paper and a mechanical-control auto filter paper feeding structure, wherein the soot sampling gun includes a gathering tube, a Pitot tube and a sheath tube.

Said soot mass detection unit comprising: a β-ray detecting means and a detected data processing means, wherein said β-ray detecting means includes a β-ray source and a β-ray receiving Geiger-Muller detector. A detected soot sample is obtained by said soot collection unit and finally the soot data are obtained by said soot mass detection unit.

The gathering tube of said soot sampling gun is equipped with an upper cavity at an end thereof and a lower cavity corresponding to the upper cavity. The filter paper passes through gap between the upper cavity and lower cavity. A filter paper supporting grid is provided at the inlet of the lower cavity. A smoke outlet is equipped at a lower part of the lower cavity. Wherein, the sampling acreage of soot acquired from the upper cavity is at least twice of the actual testing acreage of filter paper so as to reduce the sampling resistance and the mass of the soot acquired from sampling per acreage.

Preferably, the β-ray soot concentration direct-reading monitor further comprises heating-dehumidifying means including at least three heating rods which are respectively disposed on both sides of the β-ray source and one side of the sampling tube for drying the moisture contained in the soot collected by the filter paper.

Preferably, said heating-dehumidifying means further include a heating band which winds around said sampling tube and Pitot tube to bind them together and then be put into said sheath tube. Furthermore, said heating band also encircles said upper cavity to implement the heating function during the whole process to prevent condensation.

Preferably, the present invention uses a PM$^{147}$ source as the β-ray source for eliminating the affection of large diameter of the soot particulate on the measurement.

Preferably, the present invention uses a sampling tube with a diameter of 4-6 millimeters to improve the flow rate of smoke thereby preventing the deposition and absorption of the soot in said sampling tube.

Secondly, a method for determining an effective sample of soot is provided to determine whether the detected sample collected by the β-ray soot concentration direct-reading monitor is effective. This method for determining an effective sample comprises the following steps:

Step a: initiating said β-ray soot concentration direct-reading monitor,
Step b: testing detected samples after the sampling process is over to obtain the output frequencies of the β-ray receiving Geiger-Muller detector,
Step c: judging whether said output frequencies have changed, if so, going to Step d, if not, going to Step e,
Step d: testing the next group of detected samples to obtain the output frequencies of the β-ray receiving Geiger-Muller detector, and then going to Step c,
Step e: determining this group of detected samples is effective.

The advantages of the present invention lie in the improvement of measurement accuracy of soot and the prevention of interference of moisture to the soot measurement.

THE BRIEF DESCRIPTION OF FIGURES

DETAILED DESCRIPTION OF EMBODIMENTS

In combination with the Figures, the above-mentioned and other technical features and advantages of the present invention are expounded in the following.

Figure 1:
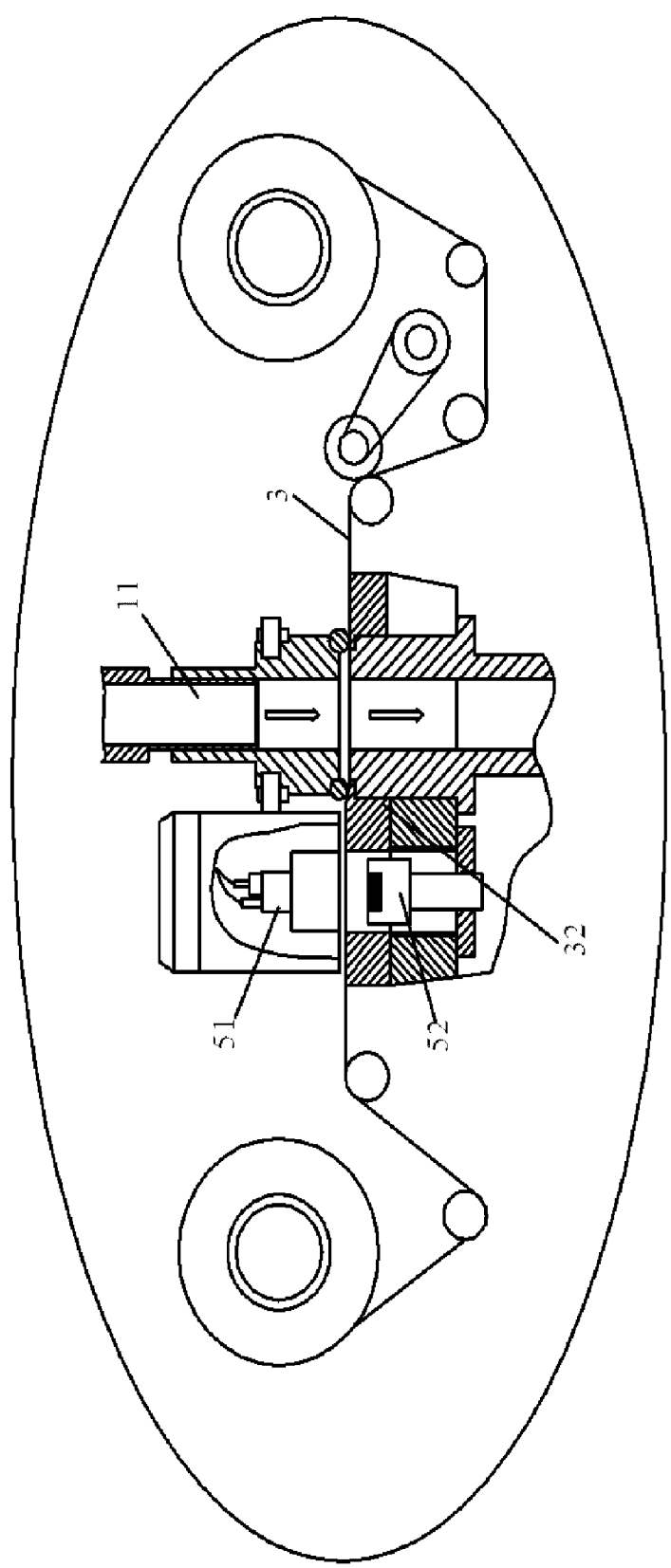
FIG. 1 shows a diagram of internal structure of a β-ray soot concentration direct-reading monitor in the prior art.
Figure 2:
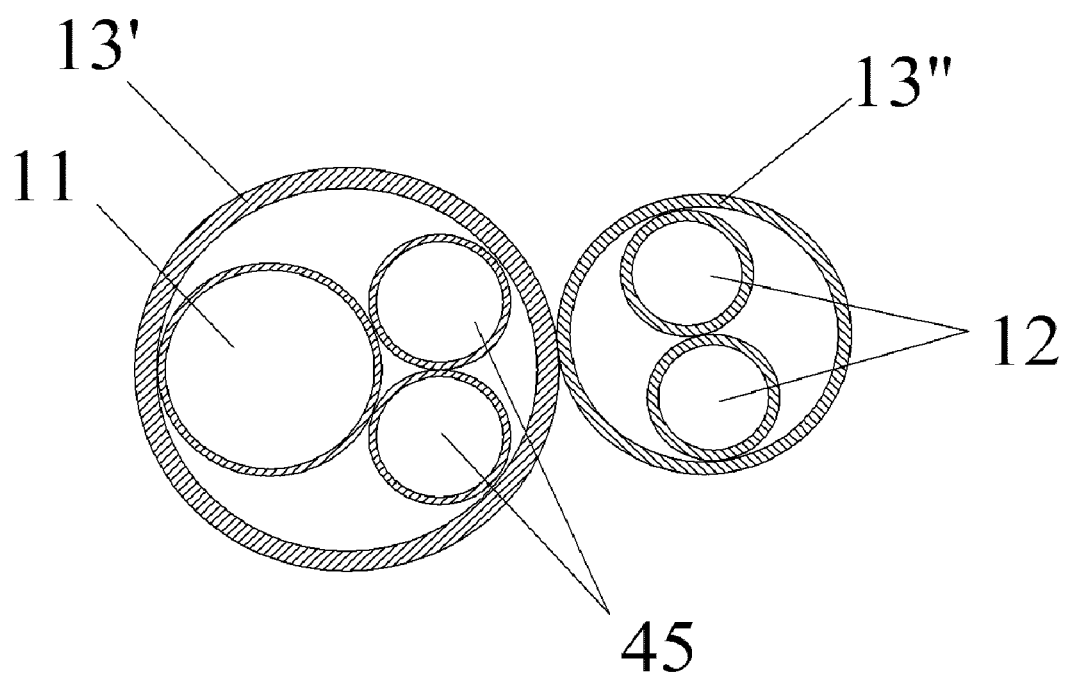
FIG. 2 shows a structural diagram of a sampling gun of a β-ray soot concentration direct-reading monitor in the prior art.
Figure 3:
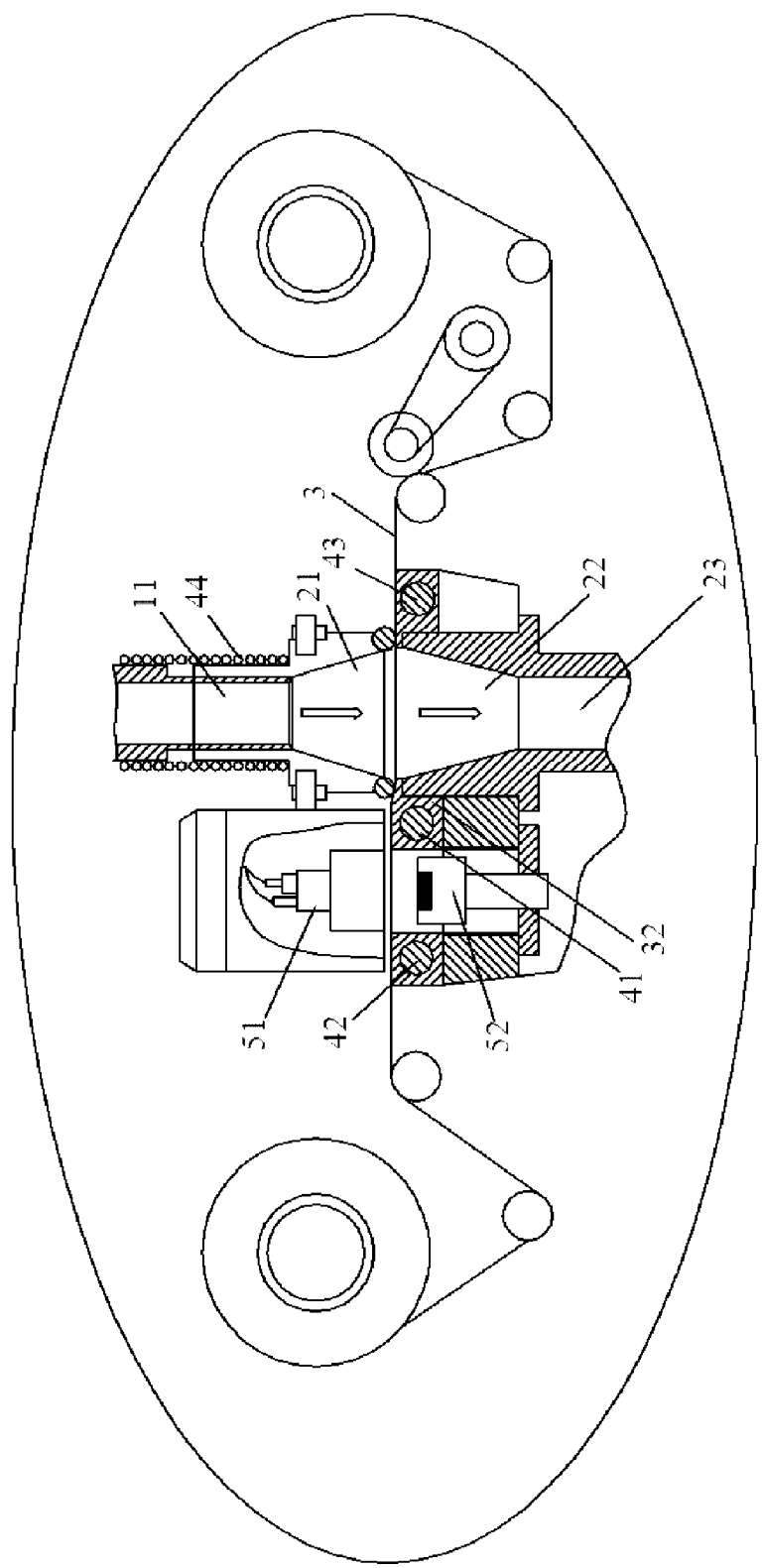
FIG. 3 shows a diagram of internal structure of the β-ray soot concentration direct-reading monitor of the present invention.

With reference to FIG. 3, it is a diagram of the internal structure of the β-ray soot concentration direct-reading monitor of the present invention. The monitor of the present invention has a structure similar to the general structure of a β-ray soot concentration direct-reading monitor in the prior art, namely comprises: a soot collection unit and a soot mass detection unit, said soot collection unit includes a soot sampling gun, a filter paper and mechanical-control auto filter paper feeding structure, wherein the soot sampling gun includes a gathering tube 11, a Pitot tube 12 and a sheath tube 13. Said soot mass detection unit comprises: β-ray detecting means and detected data processing means (not shown in Figures), wherein said β-ray detecting means includes a β-ray source 52 and a β-ray receiving Geiger-Muller detector, 51. A detected soot sample is obtained by said soot collection unit and finally the soot data is obtained by said soot mass detection unit.

Compared with the prior art, the present invention makes some adjustments to the soot collection unit and the soot mass detection unit with the purpose of improving the measurement accuracy.

First of all, the present invention adopts following technical solution to avoid the mass overflow per sampling acreage which causes β-ray gauge fails. The gathering tube of said soot sampling gun is equipped at an end thereof with an upper cavity 21 and a lower cavity 22 corresponding to the upper cavity 21, said filter paper 3 passes through gap between the upper cavity and lower cavity, a paper supporting grid 23 is provided at the inlet of the lower cavity 22, and a smoke outlet 23 is equipped at a lower part of the lower cavity. Wherein the sampling acreage of soot acquired from the upper cavity 21 is at least twice of the actual testing acreage 31 of filter paper so as to reduce the sampling resistance and the mass of the acquired soot per acreage. The results as above mentioned are achieve by the structure of a broad bugle shape.

Figure 4:
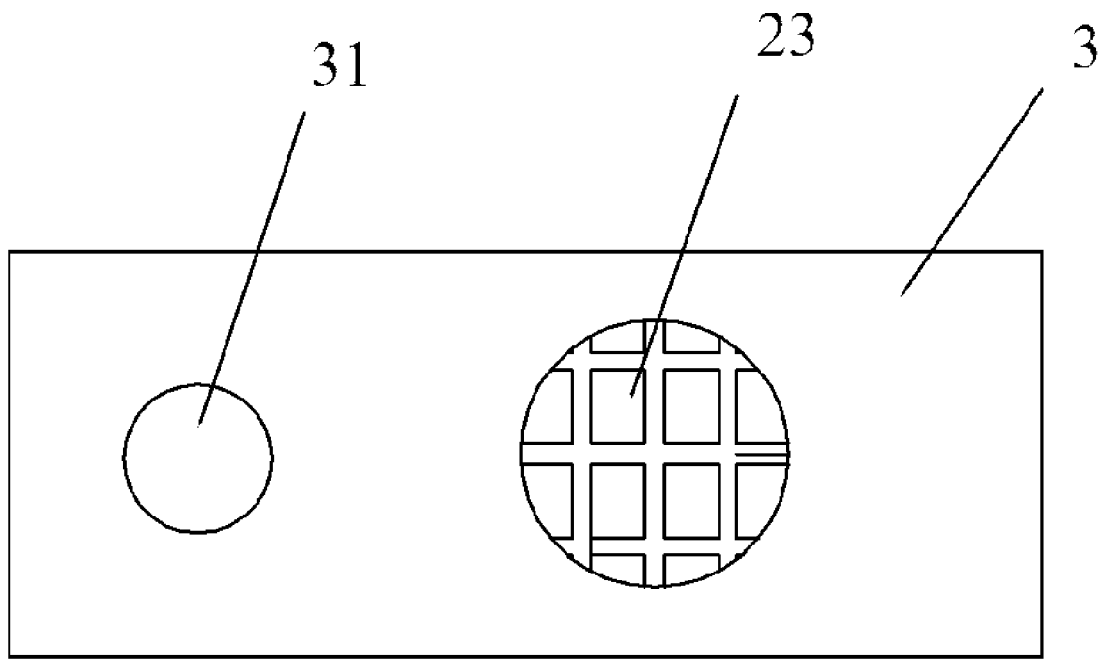
FIG. 4 shows a comparative view between the sampling acreage and testing acreage during the sampling process of filter paper.

With reference to FIG. 4, it is a comparative view between the sampling acreage and the testing acreage during the sampling cycle of the filter paper in the present invention. It can be seen from FIG. 4 that the sampling acreage of the soot acquired from the upper cavity 21 is at least twice of the actual testing acreage 31 of filter paper in the case of the filter paper being taken as the carrier of actual sampling and soot detection. Such solution solves the problem of mass overflow per sampling acreage which leads to the failure of β-ray gauge. Since β-ray is a low energy source, it can scarcely penetrate the mass per acreage over 1.5-2.0 mg/cm$^2$. By means of this configuration, the above technical problem has been solved. In addition, this configuration also greatly reduces the resistance of smoke line during the sampling and thus solves the problem of sample extraction and transport (flux following). If sampling according to the initial sampling acreage is going on, then the sampling is unable to be continued because of the rapid increase of the resistance.

Figure 5:
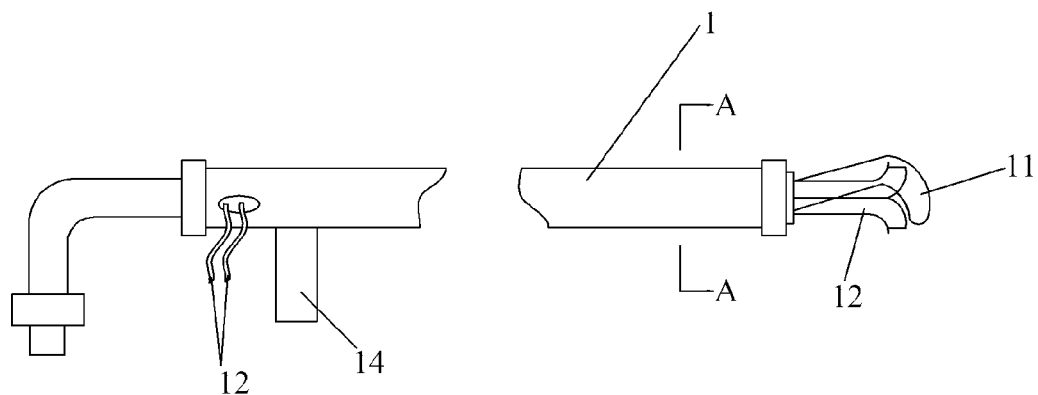
FIG. 5 shows a structural diagram of the sampling gun of the β-ray soot concentration direct-reading monitor of the present invention.
Figure 6:
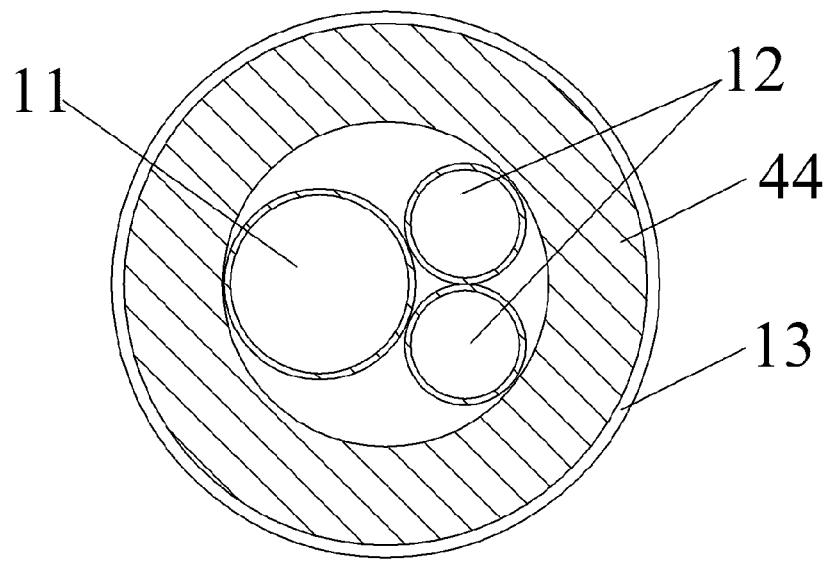
FIG. 6 shows a sectional view of the sampling gun of the β-ray soot concentration direct-reading monitor of the present invention.

Secondly, in order to prevent the moisture contained in the soot from bringing disadvantages to the measurement, a heating-dehumidifying means is introduced into the structure design. The heating-dehumidifying means includes three heating rods 41, 42, 43 and a heating band 44, wherein as depicted in FIG. 3, the heating rods 41, 42, 43 can be multiplied by groups to achieve a better drying effect. Said heating rods 41, 42, 43 are all located in a supporting block 32 of the sampling filter paper, two of which are respectively disposed at both sides of the β-ray source 52, and another is located at one side of the sampling tube 11. When the filter paper 3 is moving over the heating rods, the heating rods parch the moisture contained in the soot collected by the filter paper 3 to avoid a hazard of unreliable measurement caused by the moisture content. The usage of the heating band 44 is introduced in the following with reference to FIG. 5 and FIG. 6, which respectively are the structural diagram and the sectional view of the β-ray soot concentration direct-reading monitor of the present invention. Said Pitot tube 12 and said sampling tube 11 are bound together by winding said heating band 44 around said Pitot tube 12 and sampling tube 12 and put into said sheath tube 13. Said heating band 44 also encircles said upper cavity 21 to heat the soot during the whole process so as to prevent condensation. The heating temperature generally ranges from 120 Celsius degree to 200 Celsius degree.

Thirdly, as for the design of the caliber of sampling tube 11, the present invention chooses the sampling tube 11 with 4-6 millimeters diameter for the purpose of increasing gas flow rate and preventing the deposition and absorption of the soot in said sampling tube 11.

Fourthly, as for the selection of the β-ray source 52, a $C^{14}$ source is not suitable for the soot detection though the present available β-ray dust monitors all use the $C^{14}$ source as the detection source as is described precedingly. The $C^{14}$ source is of relatively low energy, only 0.155 Mev and has a poor penetration ability, only 1.5-2.0 $mg/cm^2$. However, the mass of the filter paper usually used in the monitors is about 6-8 $mg/cm^2$, and the soot allowed to be sampled shall be smaller than 2 $mg/cm^2$. The detection of such soot with high dispersion and large particulate is not accurate because the β-ray cannot penetrate at all and are absorbed by the soot completely. Therefore, present invention utilizes a $PM^{147}$ source, which has an energy level of 0.223 Mev and a penetration range of 0.2-20 $mg/cm^2$, which is twice as high as the $C^{14}$ source.

Figure 7:
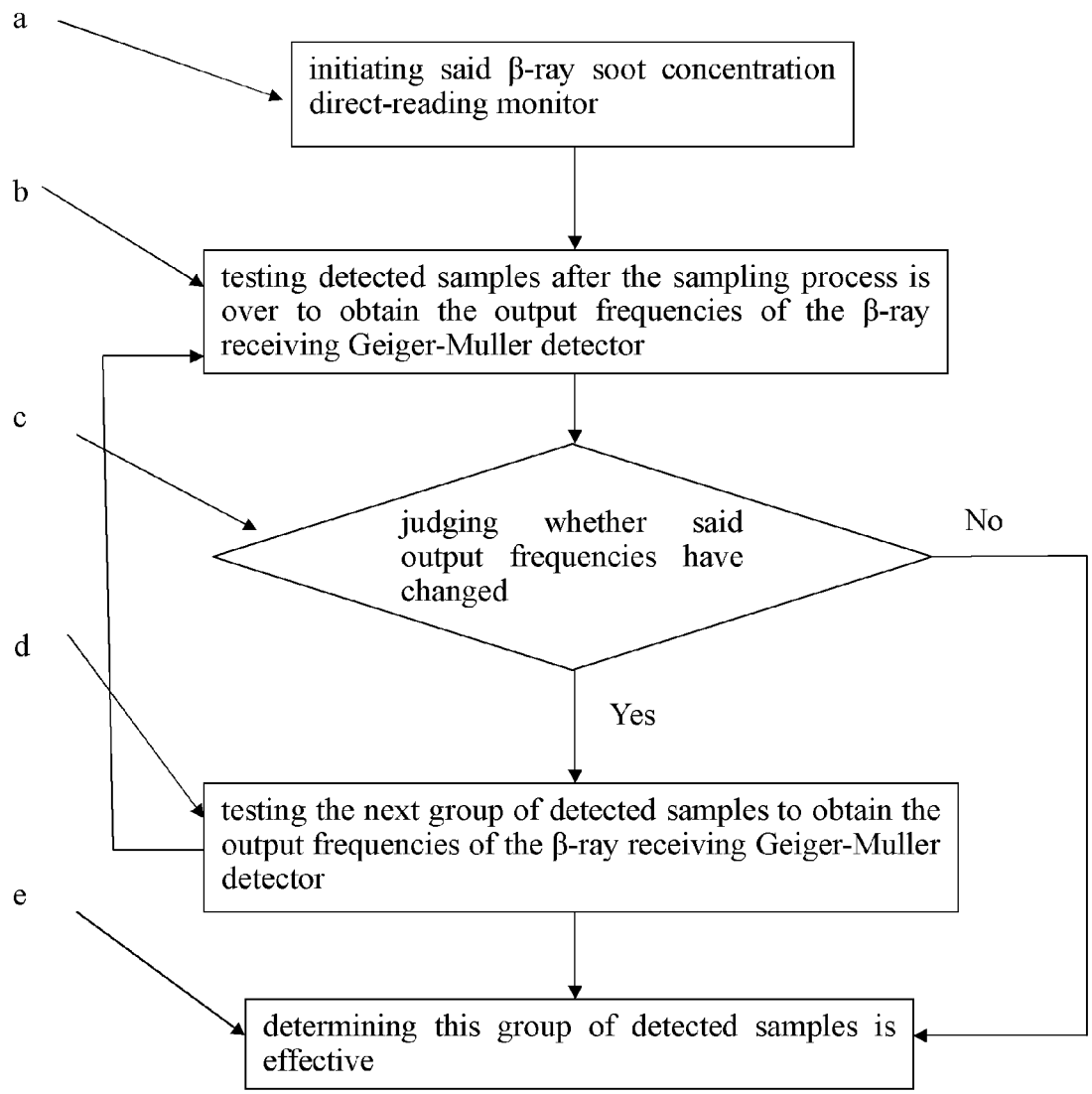
FIG. 7 shows a flow chart of the method for determining an effective soot sample employed by the β-ray soot concentration direct-reading monitor.

Finally, in order to obtain accurate soot mass effectively, the sample of the soot acquired on the filter paper is required to be effective. Namely, the moisture content shall be in the lowest level (that is to say, shall have been parched). Therefore, the present invention provide a method for determining whether the detected sample collected by said β-ray soot concentration direct-reading monitor is effective. As shown in FIG. 7, the method comprises the following steps:

Step a: initiating said β-ray soot concentration direct-reading monitor,

Step b: testing detected samples after the sampling is over to obtain the output frequencies of the β-ray receiving Geiger-Muller detector, Step c: judging whether said output frequencies have changed, if so, going to Step d, if not, going to Step e, Step d: testing the next group of detected samples to obtain the output frequencies of the β-ray receiving Geiger-Muller detector, and then go to Step c, Step e: determining this group of detected samples is effective.

The method is realized by the software controlling the mechanical-control auto feeding device and β-ray receiving Geiger-Muller detector.

To sum up, said β-ray soot concentration direct-reading monitor and the method for determining an effective sample thereof obtained by the improvement of the inventor of the present invention can undoubtedly achieve the expected technical effect and thus a patent application relating to the β-ray soot concentration direct-reading monitor and the method for determining an effective sample thereof is submitted in accordance with the law.

While only preferred embodiment has been chosen to illustrate the present invention, it will be apparent to those skilled in the art from this disclosure that various changes and modifications and even equivalents can be made herein without departing from the scope of the invention as defined in the appended claims. Furthermore, the foregoing descriptions of the embodiment according to the present invention are provided for illustration only, and not for the purpose of limiting the invention as defined by appended claims and their equivalents.

The invention claimed is:

1. A β-ray soot concentration direct-reading monitor, comprising:
   a soot collection unit including:
       a soot sampling gun,
       a filter paper,
       and a mechanical-control auto filter paper feeding structure, wherein said soot sampling gun includes a gathering tube, a Pitot tube and a sheath tube; and
   a soot mass detection unit including:
       a β-ray detecting means and a detected data processing means, wherein said β-ray detecting means includes a β-ray source and a β-ray receiving Geiger-Muller detector, and a soot sample is obtained by said soot collection unit and finally the soot data are obtained by said soot mass detection unit,
   wherein the gathering tube of said soot sampling gun is equipped with an upper cavity at an end thereof and a lower cavity corresponding to the upper cavity, said filter paper passes through gap between the upper cavity and lower cavity, a filter paper supporting grid is provided at the inlet of said lower cavity, a smoke outlet is equipped at a lower part of the lower cavity, wherein the sampling area of soot acquired from the upper cavity is at least twice of the actual testing area of filter paper so as to reduce the resistance of sampling and the mass of the soot acquired from sampling per area.

2. The β-ray soot concentration direct-reading monitor according to claim 1, further comprising heating-dehumidifying means including at least three heating rods which are respectively disposed on both sides of the β-ray source and one side of the sampling tube for drying the moisture contained in the soot collected by the filter paper.

3. The β-ray soot concentration direct-reading monitor according to claim 2, wherein said heating-dehumidifying means further include a heating band which winds around said sampling tube and Pitot tube to bind them together and then to be put into said sheath tube, furthermore, said heating band also encircles said upper cavity to implement the heating function during the whole process to prevent condensation.

4. The β-ray soot concentration direct-reading monitor according to claim 1, wherein said β-ray source adopts a $PM^{147}$ source for eliminating the affection of large diameter of the soot particulate on the measurement.

5. The β-ray soot concentration direct-reading monitor according to claim 1, wherein said sampling tube has a diameter of 4-6 millimeters to improve the gas flow rate and thereby to prevent the deposition and absorption of the soot in said sampling tube.

6. A method for determining an effective sample of soot, which is used to determine whether the detected sample collected by said β-ray soot concentration direct-reading monitor is effective, comprising:
   Step a: initiating said β-ray soot concentration direct-reading monitor,
   Step b: testing detected samples after the sampling process is over to obtain the output frequencies of the β-ray receiving Geiger-Muller detector,
   Step c: judging whether said output frequencies have changed, if so, going to Step d, if not, going to Step e,
   Step d: testing the next group of detected samples to obtain the output frequencies of the β-ray receiving Geiger-Muller detector, and then going to Step c, and
   Step e: determining this group of detected samples is effective.

* * * * *